(12) United States Patent
Shimaoka et al.

(10) Patent No.: US 7,964,410 B2
(45) Date of Patent: Jun. 21, 2011

(54) METHOD FOR PREPARING ANALYSIS SAMPLE, ANALYSIS SAMPLE AND SUGAR CHAIN CAPTURE AGENT

(75) Inventors: Hideyuki Shimaoka, Tokyo (JP); Hiromitsu Kuramoto, Tokyo (JP); Shinichiro Nishimura, Hokkaido (JP); Yasuro Shinohara, Hokkaido (JP); Yoshiaki Miura, Hokkaido (JP); Jun-ichi Furukawa, Hokkaido (JP)

(73) Assignees: Sumitomo Bakelite Company, Ltd., Tokyo (JP); National University Corporation Hokkaido University, Hokkaido (JP)

( * ) Notice: Subject to any disclaimer, the term of this patent is extended or adjusted under 35 U.S.C. 154(b) by 223 days.

(21) Appl. No.: 12/224,953

(22) PCT Filed: Mar. 13, 2007

(86) PCT No.: PCT/JP2007/000214
§ 371 (c)(1),
(2), (4) Date: Sep. 10, 2008

(87) PCT Pub. No.: WO2007/108204
PCT Pub. Date: Sep. 27, 2007

(65) Prior Publication Data
US 2009/0068752 A1    Mar. 12, 2009

(30) Foreign Application Priority Data
Mar. 16, 2006 (JP) .................................. 2006-073170

(51) Int. Cl.
*G01N 33/00* (2006.01)

(52) U.S. Cl. .......... 436/94; 436/106; 436/119; 436/120; 436/174; 436/175

(58) Field of Classification Search .................. None
See application file for complete search history.

(56) References Cited

U.S. PATENT DOCUMENTS
2006/0188996 A1    8/2006   Nishimura et al.

FOREIGN PATENT DOCUMENTS
JP    2003-313197    11/2003
WO    2004/058687    7/2004

OTHER PUBLICATIONS

Shimaoka et al., "Development of S-Bio®BlotGlyco™, a Versatile Kit for High-throughput Oligosaccharide Purification Via Chemoselective Glycoblotting", Bio Industry, vol. 22, No. 11, 2005, pp. 54-59 w/ English language translation.
Lambert et al., "Purified Immunotoxins That Are Reactive with Human Lymphoid Cells", The Journal of Biological Chemistry, vol. 260, No. 11, 1985, pp. 12035-12041.
Manz et al., "Synthesis of a New Disulfide Affinity Adsorbent for Purification of Human Uterine Progesterone Receptor", Eur. J. Biochem, vol. 128, 1982, pp. 249-255.

*Primary Examiner* — Yelena G Gakh
*Assistant Examiner* — David Weisz
(74) *Attorney, Agent, or Firm* — Smith, Gambrell & Russell, LLP

(57) ABSTRACT

A method for preparing an analysis sample which involves the sugar chain capture step comprising a reaction of capturing a sugar chain and/or a sugar derivative from a biological sample by using a sugar chain capture agent and the excision step comprising excising a compound containing a moiety capturing the sugar chain and/or the sugar derivative from the sugar chain capture agent after the completion of the sugar chain capture reaction and releasing the compound.

16 Claims, 5 Drawing Sheets

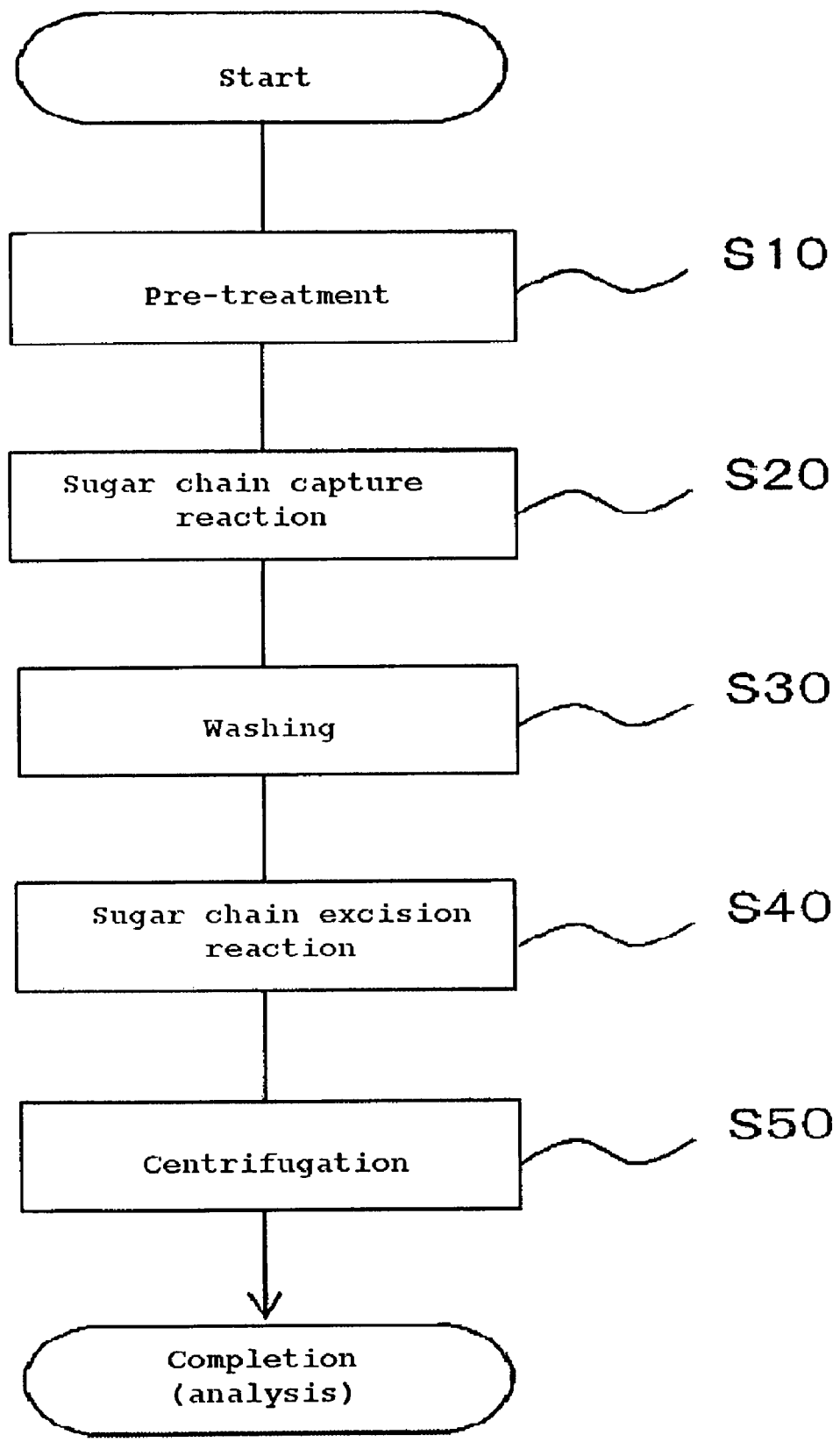
[FIG. 1]

[FIG. 2]
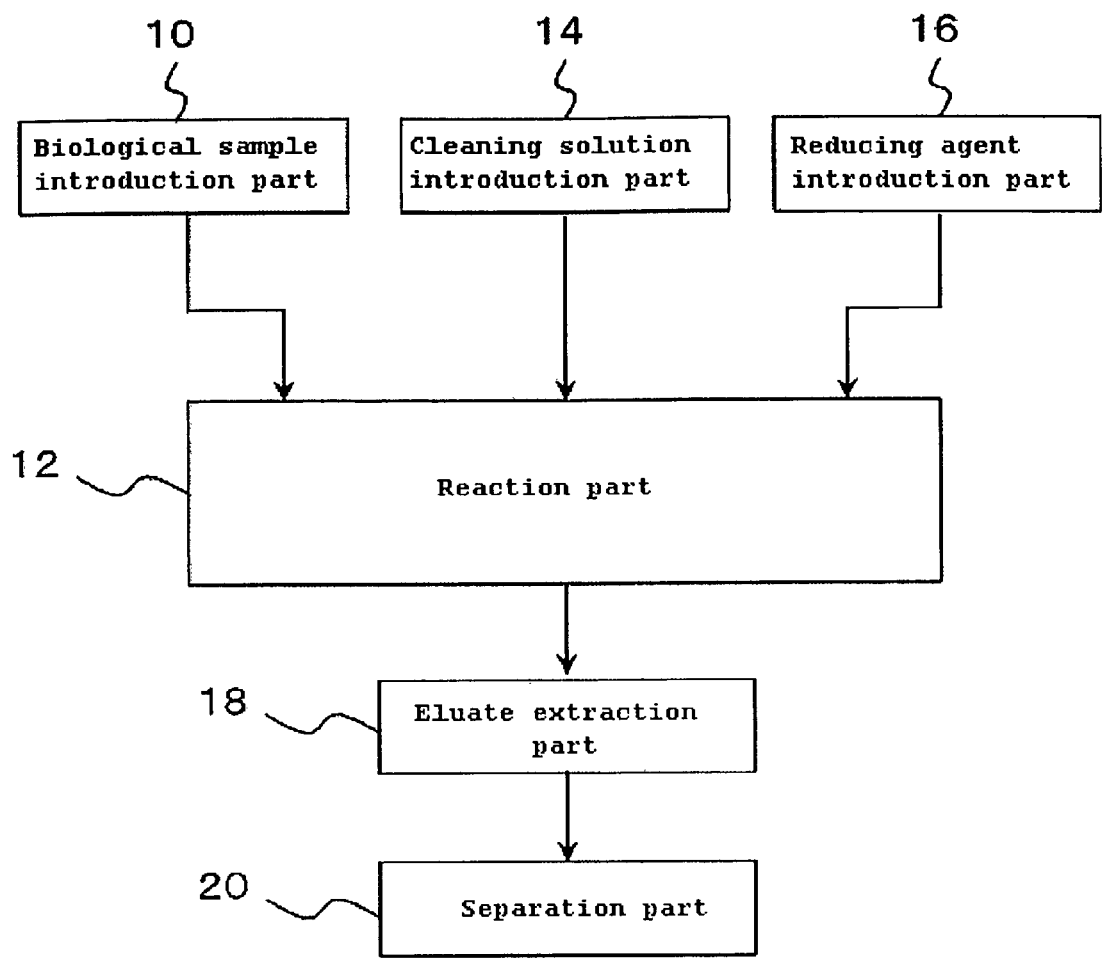

[FIG. 3]
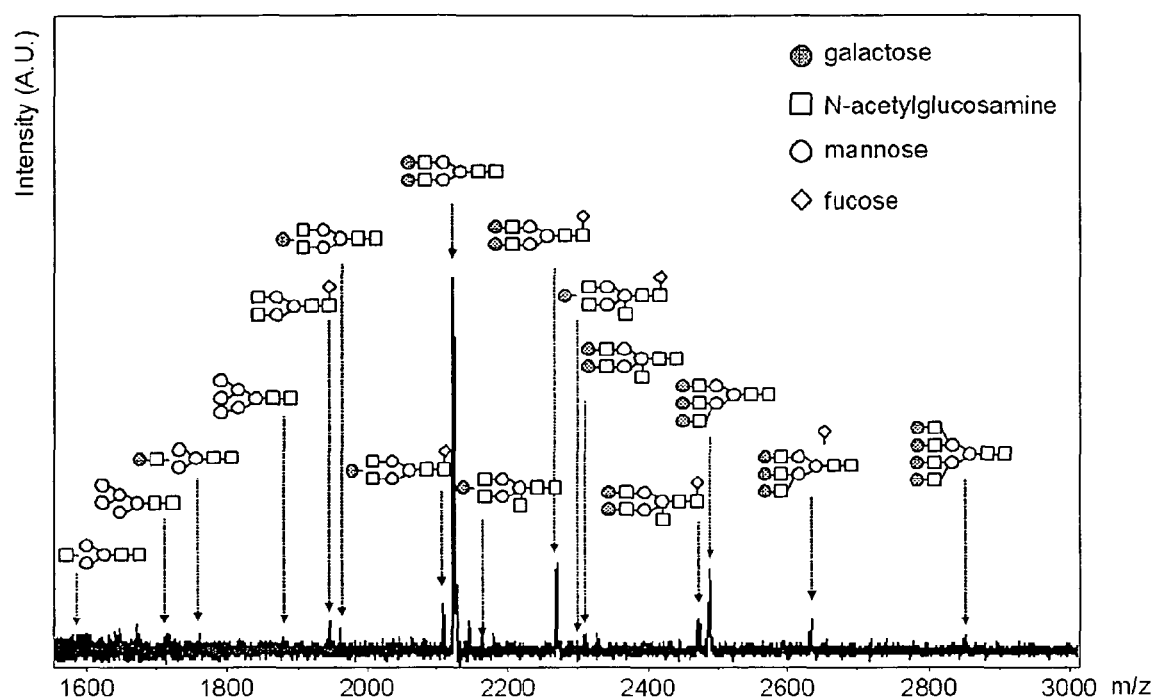

[FIG. 4]
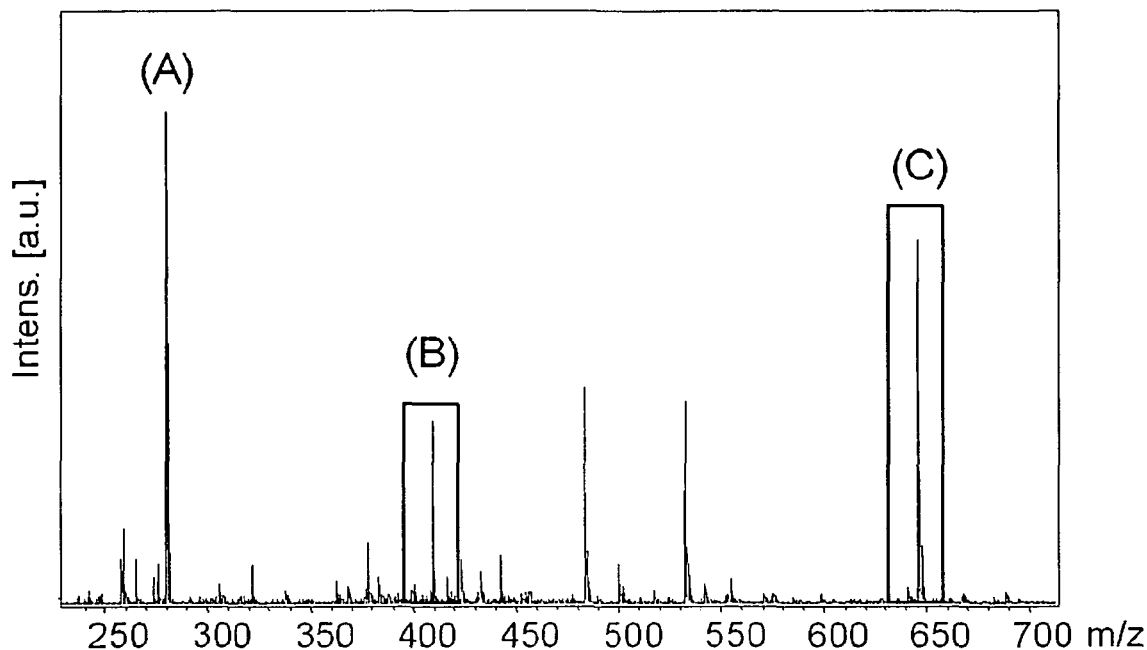
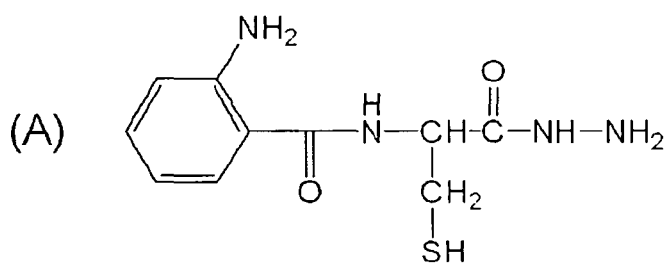
(B)   LacNAc
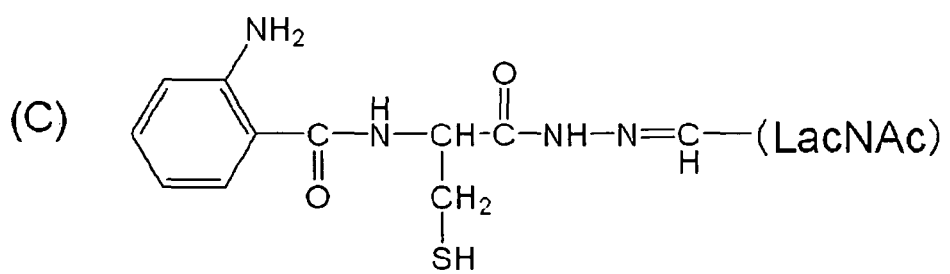

[FIG. 5]
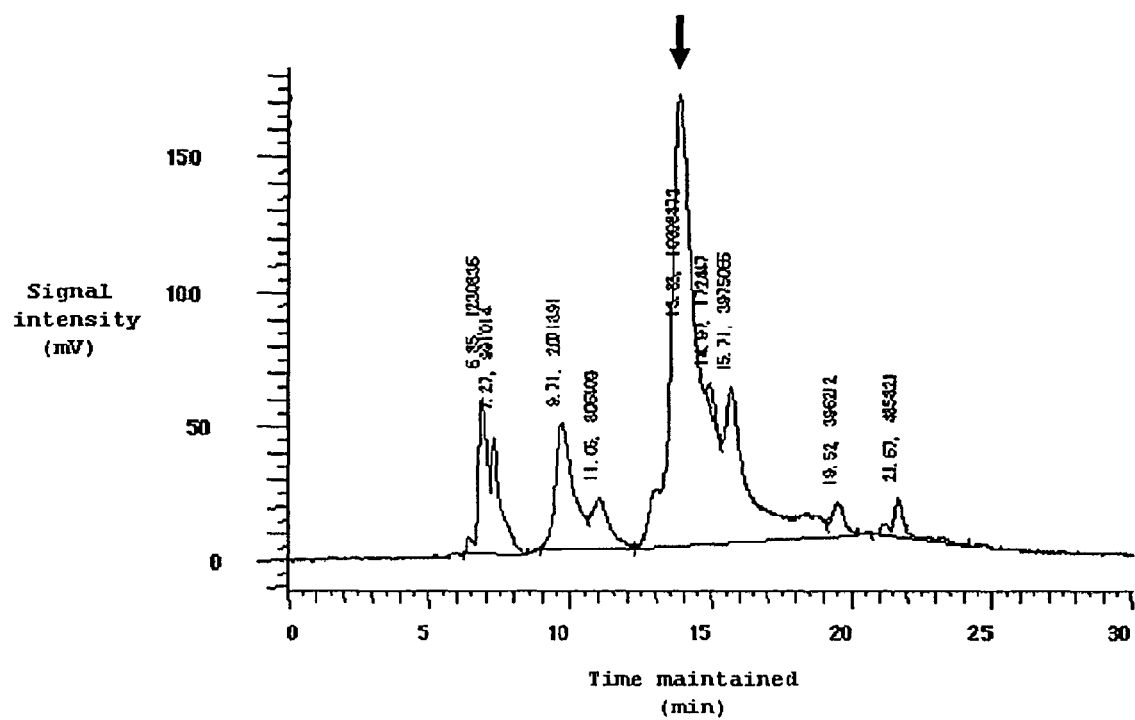

METHOD FOR PREPARING ANALYSIS SAMPLE, ANALYSIS SAMPLE AND SUGAR CHAIN CAPTURE AGENT

TECHNICAL FIELD

The present invention relates to a method for preparing an analysis sample. Particularly, the invention relates to a method for preparing an analysis sample for releasing as an analysis sample for analyzing a sugar chain from a biological sample, an analysis sample obtained by using the method for preparing an analysis sample, and a sugar chain capture agent used for the method for preparing an analysis sample.

BACKGROUND ART

A biological polymer plays an importance role in biotechnology fields such as medical science, cell engineering, organ engineering and the like. To clarify the control mechanism of the biological reaction using these substances is related to the development in the biotechnology fields.

Of biological polymers, a sugar chain is extremely rich in its diversity, and is a substance participating in various functions of an organism present in the nature. The sugar chain is present as glycoconjugate bonded to protein, lipid or the like in vivo in many cases, and is one of important components in vivo. It has become clear that the sugar chain in vivo is deeply related to information transfer between cells, regulation of functions or interaction of protein, and the like.

Incidentally, the term "sugar chain" refers to a generic term of a chain of molecules coupled with monosaccharide such as glucose, galactose, mannose, fucose, xylose, N-acetylglucosamine, N-acetylgalactosamine, sialic acid or the like and a derivative thereof by a glycosidic bond.

Examples of the biological polymer having a sugar chain include peptidoglycan of a cell wall of a plant cell contributing to the stability of cells, glycolipid affecting cell differentiation, population growth, adhesion, migration or the like, glycoprotein taking part in intercellular interaction or cellular recognition and the like. A mechanism that the sugar chains contained in these biological polymers control a high-precision biological reaction while acting for, helping, amplifying, regulating or hindering functions mutually with other biological polymers have been gradually made clear. Furthermore, when a relation between such a sugar chain and cell differentiation, population growth, cell adhesion, immunity and a malignant change (cancer) in cells becomes clear, a new development can be expected to be planned by closely relating this sugar chain engineering to the medical science, cell engineering, or organ engineering.

In Patent Document 1, there have been described a substance capable of specifically reacting with such a sugar chain, and a method of separating a sugar chain by using the substance as well.

Patent Document 1: International Publication Pamphlet No. 2004/058687

DISCLOSURE OF THE INVENTION

Problems to be Solved by the Invention

By the way, in Patent Document 1, there has been described an example using an acid treatment employing trifluoroacetic acid, acidic resin or the like in order to release (excise) the sugar chain captured by the sugar chain capture agent from the sugar chain capture agent. To expose the sugar chain under such several conditions may cause degeneration of the sugar chain such as separation of a sialic acid residue having a property of being bonded to a terminal end of the sugar chain that is taken out from the biological sample, and a property of being easily separated under acidic conditions so that it has been demanded that excision of the sugar chain is carried out under much milder conditions. Incidentally, the existence of the sialic acid to be bonded to the sugar chain and the bonding site are related to the disease in many cases so that it has been demanded that the sugar chain is analyzed in the perfect state of the sialic acid. When even a part of the sialic acid is separated at the pre-treatment step before analysis, accurate information of the sugar chain cannot be obtained.

Then, an object of the present invention is to provide a method for preparing an analysis sample which enables to capture a sugar chain using a sugar chain capture agent when the sugar chain for an analysis sample is recovered and purified from a biological sample containing a sugar chain and to excise this sugar chain under mild conditions, an analysis sample obtained by applying this method, and a sugar chain capture agent to be used for the preparation of the analysis sample.

Means for Solving the Problems

A method for preparing an analysis sample according to the present invention involves the sugar chain capture step including a reaction of capturing a sugar chain and/or a sugar derivative from a biological sample by using a sugar chain capture agent, and the excision step including excising a compound containing a moiety capturing the sugar chain and/or the sugar derivative from the sugar chain capture agent after the completion of the sugar chain capture reaction and releasing the compound.

Furthermore, a method for preparing an analysis sample according to the present invention involves the sugar chain capture step including a reaction of capturing a sugar chain and/or a sugar derivative from a biological sample by using a sugar chain capture agent, the washing step including washing the sugar chain capture agent after the completion of the sugar chain capture reaction, and the excision step including excising a compound containing a moiety capturing the sugar chain and/or the sugar derivative from the sugar chain capture agent after the completion of washing and releasing the compound.

In the aforementioned method for preparing an analysis sample, the sugar chain capture agent can be immobilized to a carrier through a disulfide bond, and the excision step can include a reaction of cutting off this disulfide bond.

Or, in the aforementioned method for preparing an analysis sample, the sugar chain capture agent used in the sugar chain capture step may have a structure represented by the following formula (1), (Carrier)-S—S-L-A     (1)

wherein, in the formula, the carrier is an inorganic substance or an organic polymer substance free from contributing to the sugar chain capture reaction; L is a linker region; A is a capture region capturing a sugar chain; and —S—S— is a disulfide bond.

Furthermore, in this method for preparing an analysis sample, the capture region A can be either of an aminooxy group or a hydrazide group. Further, the linker region L may contain a moiety consisting of at least one of arginine, tryptophan, phenylalanine, tyrosine, cysteine and a derivative thereof.

Furthermore, in the aforementioned method for preparing an analysis sample, the sugar chain capture agent may have a structure of the following formula (2),

[Chemical Formula 1]

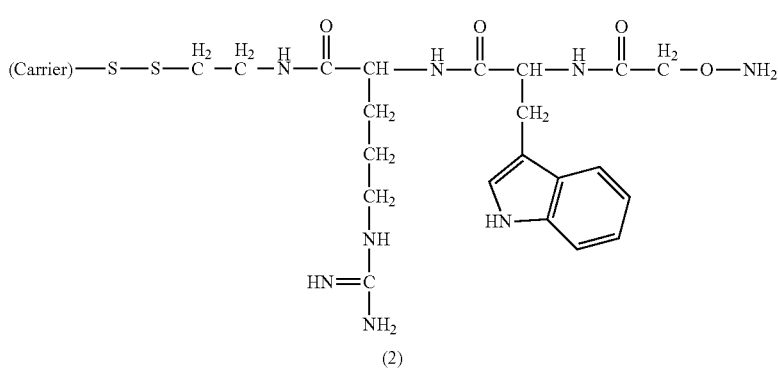

(2)

wherein, in the formula, the carrier is an inorganic substance or an organic polymer substance free from contributing to the sugar chain capture reaction.

In the aforementioned method for preparing an analysis sample, the linker region L of the sugar chain capture agent may include a moiety containing chromophore or fluorophore. Furthermore, the linker region L of the sugar chain capture agent may contain a cysteine residue and a 2-aminobenzoyl group.

Furthermore, in this method for preparing an analysis sample, the sugar chain capture agent may have a structure of the following formula (3),

[Chemical Formula 2]

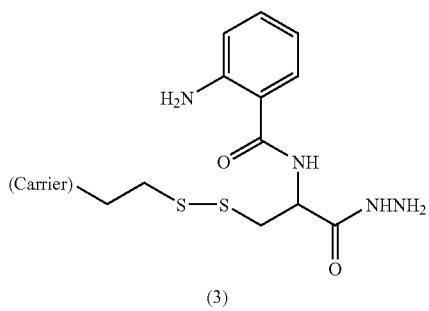

(3)

wherein, in the formula, the carrier is an inorganic substance or an organic polymer substance free from contributing to the sugar chain capture reaction.

Furthermore, in the aforementioned method for preparing an analysis sample, the sugar chain capture agent may have a structure of the following formula (4),

[Chemical Formula 3]

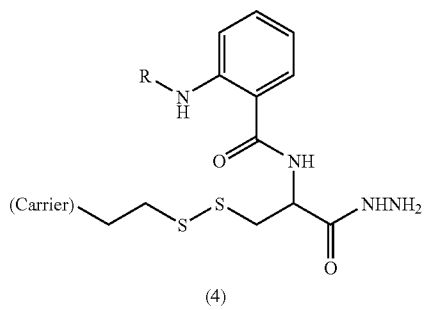

(4)

wherein, in the formula, R is a functional group capable of introducing via an amino group; and the carrier is an inorganic substance or an organic polymer substance free from contributing to the sugar chain capture reaction.

Furthermore, in the method for preparing an analysis sample, the sugar chain capture agent may have a structure of the following formula (5) or (6),

[Chemical Formula 4]

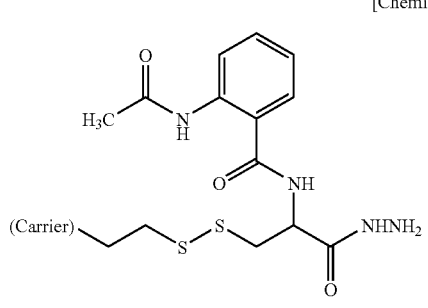

(5)

-continued

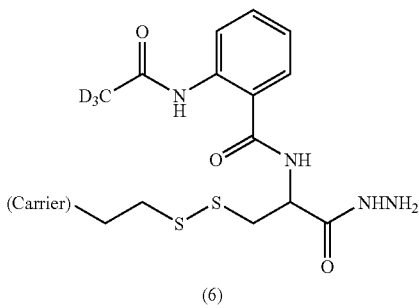

(6)

Furthermore, in the aforementioned method for preparing an analysis sample, the linker region L can be an alkyl chain or a group comprising a group containing an ester bond or an amide bond which is not labeled. Furthermore, the linker region L may have a structure represented by the following formula or combined structures of a plurality of structures freely selected from structures represented by the following formula,

[Chemical Formula 5]

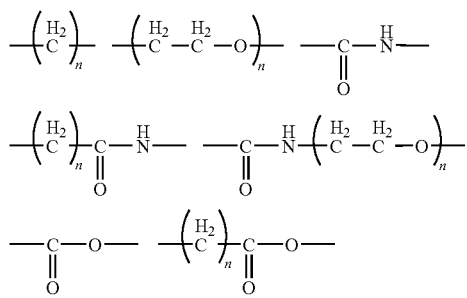

-continued

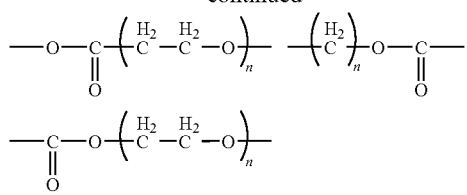

Also, in the aforementioned method for preparing an analysis sample, the disulfide bond may be cut off by the action of a reducing agent in the excision step.

Further, in the aforementioned method for preparing an analysis sample, the reaction of the sugar chain capture agent with the biological sample conducted in the sugar chain capture step may be carried out in the condition of pH 4 to 8.

Further, in any one of the aforementioned methods for preparing an analysis sample, the reaction of excising the compound containing a moiety capturing the sugar chain and/or the sugar derivative from the sugar chain capture agent conducted in the excision step may be carried out in the near-neutral pH condition.

Further, in the aforementioned method for preparing an analysis sample, the carrier in the formula (1) may be a particle.

Further, in the aforementioned method for preparing an analysis sample, the carrier in the formula (1) may be a substance to be directly bonded to a solid phase substrate or a surface of the solid phase substrate.

An analysis sample according to the present invention can be prepared and obtained from a biological sample according to any one of the aforementioned methods for preparing an analysis sample.

A sugar chain capture agent according to the present invention has a structure represented by the following formula (1), (Carrier)-S—S-L-A    (1)

wherein, in the formula, the carrier is an inorganic substance or an organic polymer substance free from contributing to the sugar chain capture reaction; L is a linker region; A is a capture region capturing the sugar chain; and —S—S is a disulfide bond.

In the sugar chain capture agent, the capture region A can be either of an aminooxy group or a hydrazide group. Further, the linker region L may contain a moiety consisting of at least one of arginine, tryptophan, phenylalanine, tyrosine, cysteine and a derivative thereof.

Or, the aforementioned sugar chain capture agent may have a structure of the following formula (2),

[Chemical Formula 6]

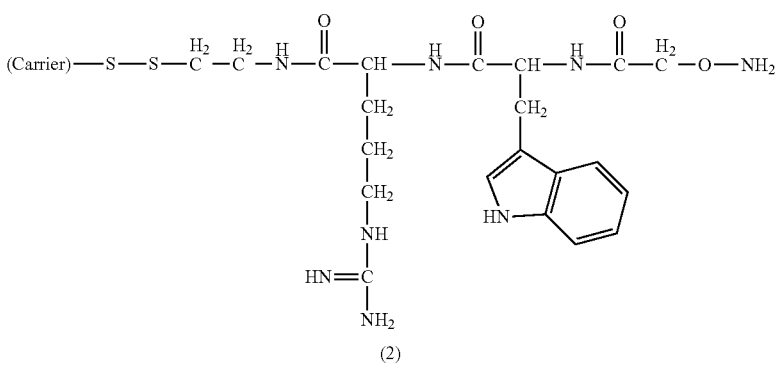

(2)

wherein, in the formula, the carrier is an inorganic substance or an organic polymer substance free from contributing to the sugar chain capture reaction.

Further, in the aforementioned sugar chain capture agent, the linker region L may have a moiety containing chromophore or fluorophore. Furthermore, the linker region L may contain a cysteine residue and a 2-aminobenzoyl group.

Further, the aforementioned sugar chain capture agent may have a structure of the following formula (3),

[Chemical Formula 7]

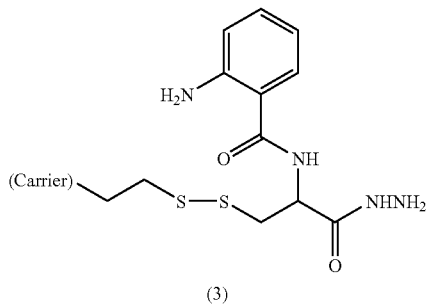

(3)

wherein, in the formula, the carrier is an inorganic substance or an organic polymer substance free from contributing to the sugar chain capture reaction.

Further, the aforementioned sugar chain capture agent may have a structure of the following formula (4),

[Chemical Formula 8]

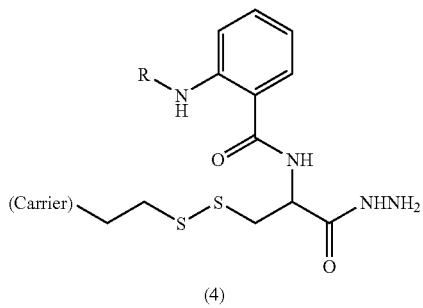

(4)

wherein, in the formula, R is a functional group capable of introducing via an amino group; and the carrier is an inorganic substance or an organic polymer substance free from contributing to the sugar chain capture reaction.

Further, the sugar chain capture agent may have a structure of the following formula (5) or (6),

[Chemical Formula 9]

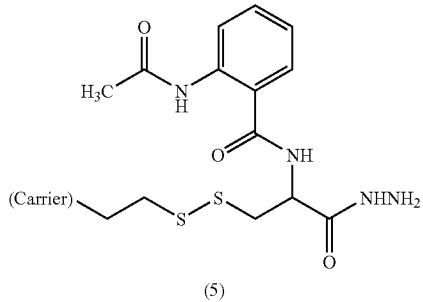

(5)

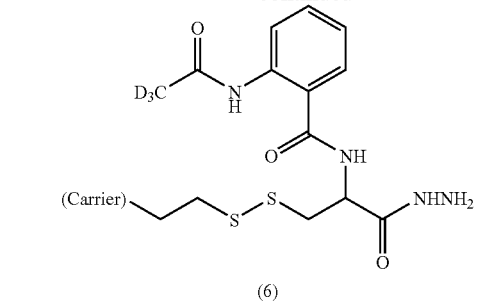

(6)

Further, in the aforementioned sugar chain capture agent, the linker region L can be an alkyl chain or a group having a group containing an ester bond or an amide bond which is not labeled. Furthermore, the linker region L may have a structure represented by the following formula or combined structures of a plurality of structures freely selected from structures represented by the following formula,

[Chemical Formula 10]

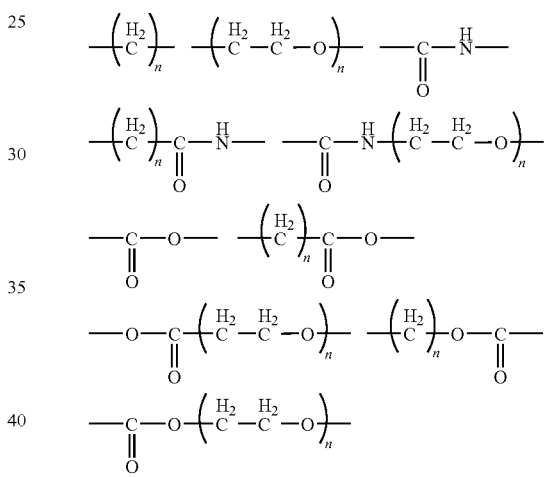

Furthermore, in the aforementioned sugar chain capture agent, the carrier in the formula (1) may be a particle.

Further, in the aforementioned sugar chain capture agent, the carrier in the formula (1) may be a substance directly bonded to a solid phase substrate or a surface of the solid phase substrate.

Effect of the Invention

According to the present invention, when a sugar chain for an analysis sample is recovered and purified from a biological sample containing a sugar chain, the sugar chain is captured by using a capture agent, thus enabling to carry out excision of this sugar chain under mild conditions.

BRIEF DESCRIPTION OF THE DRAWINGS

The above and other objects, features and advantages will be apparent from the following detailed description of the preferred embodiments in conjunction with the accompanying drawings.

FIG. 1 is a flow chart illustrating the procedure of the embodiment of the method for preparing an analysis sample according to the present invention.

FIG. 2 is a block diagram illustrating a device to which the method for preparing an analysis sample according to the embodiment is applied.

FIG. 3 is a view illustrating a chart of MALDI-TOF-MS of a compound containing a capture region capturing the sugar chain obtained in Experimental Example.

FIG. 4 is a view illustrating a chart of MALDI-TOF-MS of the compound containing a capture moiety capturing a sugar chain obtained in Experimental Example.

FIG. 5 is a graph illustrating a separation pattern of a desired product obtained in FIG. 4 by HPLC.

BEST MODE FOR CARRYING OUT THE INVENTION

The method for preparing an analysis sample of the present invention, the analysis sample obtained by applying this method, and the sugar chain capture agent used in this method will be illustrated in detail below.

FIG. 1 is a flow chart illustrating the procedure of capturing, recovering and purifying the sugar chain as an embodiment of the method for preparing an analysis sample of the present invention.

This embodiment contains Step S20 as a sugar chain capture step including a reaction of capturing the sugar chain and/or the sugar derivative (hereinafter simply referred to as a "sugar chain" in some cases) from a biological sample using a sugar chain capture agent, Step S30 as a washing step including washing the sugar chain capture agent after the completion of the sugar chain capture reaction, and Step S40 as an excision step including excising a compound containing a moiety capturing the sugar chain from the sugar chain capture agent after the completion of washing and releasing the compound.

Hereinafter, each step illustrated in FIG. 1 will be explained.

In Step S10, the pre-treatment for the recovery and purification of the sugar chain from a prescribed biological sample containing a sugar chain and/or a sugar derivative, for example, complex molecule having a sugar chain such as glycoprotein, glycopeptide, glycolipid or the like is carried out.

Herein, derivation of the biological sample is not restricted as long as the biological sample is a material to which a bio-derived sugar chain is bonded or attached. Regardless of animals, plants, bacteria, virus or culture cells, preferable examples thereof include animal-derived body fluids such as whole blood, blood plasma, human serum, sweat, saliva, urine, pancreatic juice, amniotic fluid and cerebrospinal fluid; and animal-derived tissues such as samples obtained from the biopsy diagnosis or surgical operation. Furthermore, examples of the biological sample include samples which are not separated from an individual in advance, for example, a mucous membrane tissue to which a reagent solution can be connected from the outside, or glandular tissue, and preferably epithelium of tube tissue belonging to mammary gland, prostate, pancreas.

Furthermore, examples of the pre-treatment for the biological sample include glucosidase treatment, hydrazine decomposition and, as necessary, protease treatment, cellylsis, degreasing treatment and heat denaturalization treatment. The sample obtained by subjecting the biological sample to a pre-treatment is obtained in a state of a solution, a dispersion, a suspension or a dried product. Incidentally, the pre-treated biological sample may be used in the next step as it is, or may be used in the next step while it is once dried and dissolved in a desired solution.

In Step S20, using the pre-treated biological sample obtained in Step S10, a sugar chain capture reaction of capturing a sugar chain by a specific sugar chain capture agent is carried out.

Herein, the sugar chain capture reaction, that is, a reaction of the sugar chain capture agent with the pre-treated biological sample, is carried out by introducing the sugar chain capture agent into the pre-treated sample. The reaction is carried out in the reaction system under conditions of pH of from 4 to 8, the reaction temperature of from 4 to 90 degree centigrade, preferably from 25 to 90 degree centigrade and more preferably from 40 to 90 degree centigrade for 10 minutes to 24 hours, preferably 10 minutes to 8 hours and more preferably 10 minutes to 2 hours.

The sugar chain capture agent used in this reaction is a substance having an aminooxy group or a hydrazide group, and this aminooxy group or hydrazide group is reacted with an aldehyde group and form a specific and stable bond in an equilibrium between the cyclic hemiacetal type and the non-cyclic aldehyde type, which are formed by sugar chains in fluids such as an aqueous solution or the like, thus enabling to capture the sugar chain. For example, in case of an aminooxy group, the sugar chain capture reaction refers to a reaction as shown below,

[Chemical Formula 11]

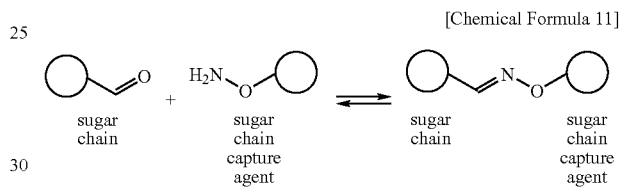

The sugar chain capture agent is immobilized to a carrier through a disulfide bond, while, as described below, in the excision step (Step S40), this disulfide bond is preferably cut off.

Concrete examples of such a sugar chain capture agent include those having a structure represented by the following formula (1), (Carrier)-S—S-L-A (1)

wherein, in the formula, the carrier is an inorganic substance or an organic polymer substance free from contributing to the sugar chain capture reaction; L is a linker region; A is a capture region capturing the sugar chain; and —S—S is a disulfide bond.

As described above, A is an aminooxy group or a hydrazide group, and, as described above, is reacted with an aldehyde group in an equilibrium between the cyclic hemiacetal type and the non-cyclic aldehyde type of the sugar chain, for functioning as a capture region capturing the sugar chain.

The linker region L represents a linker region connecting a capture region A and a region of the disulfide bond.

First, as the linker region L, there can be exemplified groups containing a moiety selected from peptide, oligopeptide and a derivative thereof. The linker region L may contain, for example, a moiety consisting of at least one of arginine, tryptophan, phenylalanine, tyrosine, cysteine and a derivative thereof.

As oligopeptide, particularly dipeptide (dimer) containing at least one of arginine, tryptophan, phenylalanine, tyrosine and cysteine is preferable. Tripeptide or higher peptide (trimer) may be good.

Furthermore, as the derivative of peptide or oligopeptide, there can be exemplified those containing at least one of derivatives of arginine, tryptophan, phenylalanine, tyrosine, cysteine and other amino acids; those with a part of the element constituting these compounds being a heavy element.

In the formula (1), L can be, for example, a linker region composed of dipeptide, and examples thereof include -arginine(R)-tryptophan(W)—, —R-phenylalanine(F)—, —R-tyrosine(Y)—, —R-cysteine(C)— and the like. As a typical example thereof, in the following formula (2), L represents a compound having a structure represented by —R—W—,

[Chemical Formula 12]

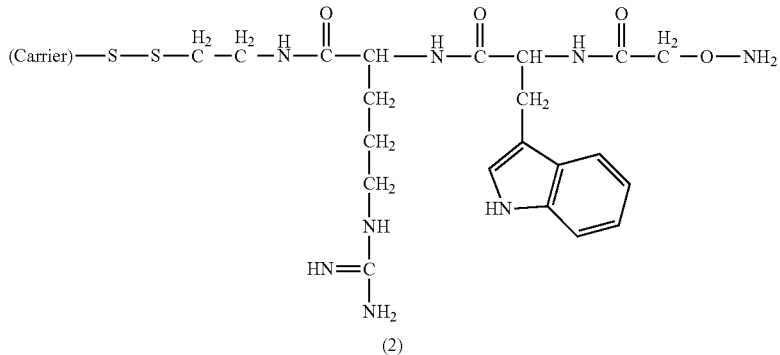

(2)

wherein, in the formula, the carrier is an inorganic substance or an organic polymer substance free from contributing to the sugar chain capture reaction.

There have been known that when an arginine (R) residue is inserted in the linker region L, the ionization is accelerated at the measurement of MALDI-TOFMS, and the detection sensitivity is improved. Furthermore, from the fact that tryptophan (W) is a fluorescent amino acid and is hydrophobic, improvement of isolation by the reverse phase HPLC and improvement of fluorescence detection sensitivity can be attempted. Incidentally, when phenylalanine and tyrosine are used, such an analysis sample is suitable for detection by UV absorption.

Further, when cysteine is used, the cysteine residue can be acted as a bonding moiety with a carrier as described later so that there is no need to carry out a reaction of introducing a thiol group such as a reaction using 2-mercaptoethylamine (compound (f)) conducted in the following Scheme 1.

The compound represented by the formula (2) can be obtained first by producing a compound (h) having a capture region and a linker region, as shown in the following Scheme 1, and subsequently, in Scheme 2, reacting with a carrier bonded, for example, to activated thiol sepharose, (Scheme 1)

[Chemical Formula 13]

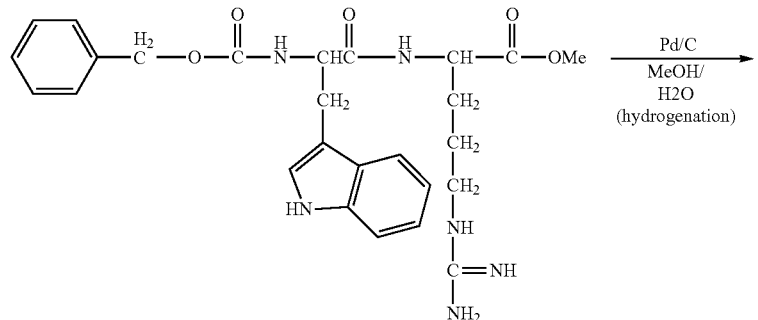

(a)

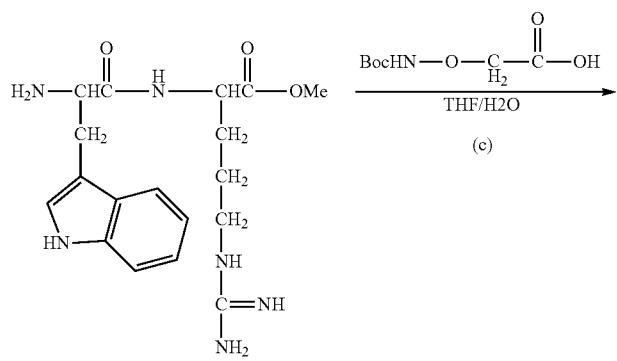
(b)
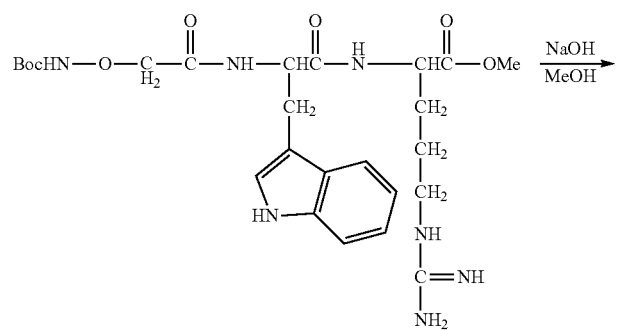
(d)
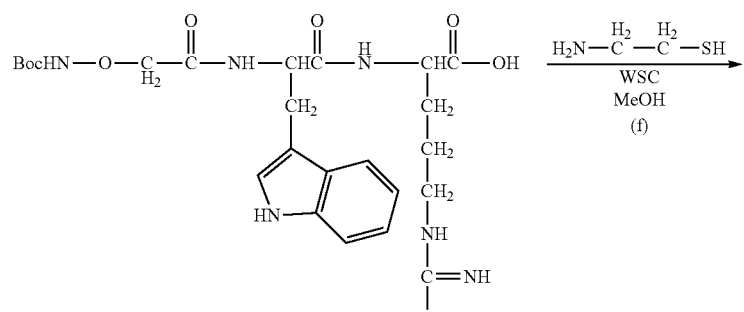
(e)
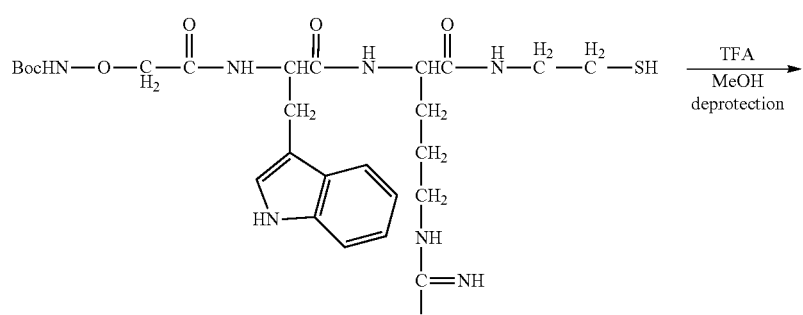
(g)

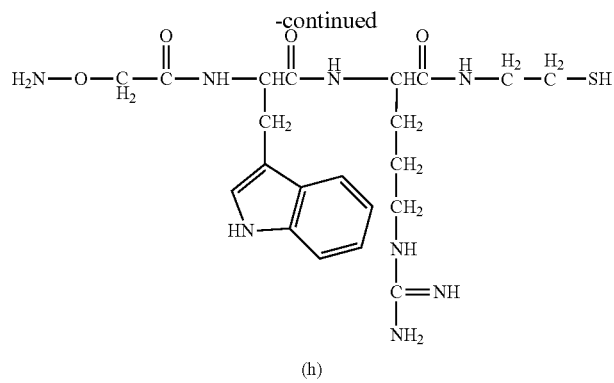

(h)

(Scheme 2)

[Chemical Formula 14]

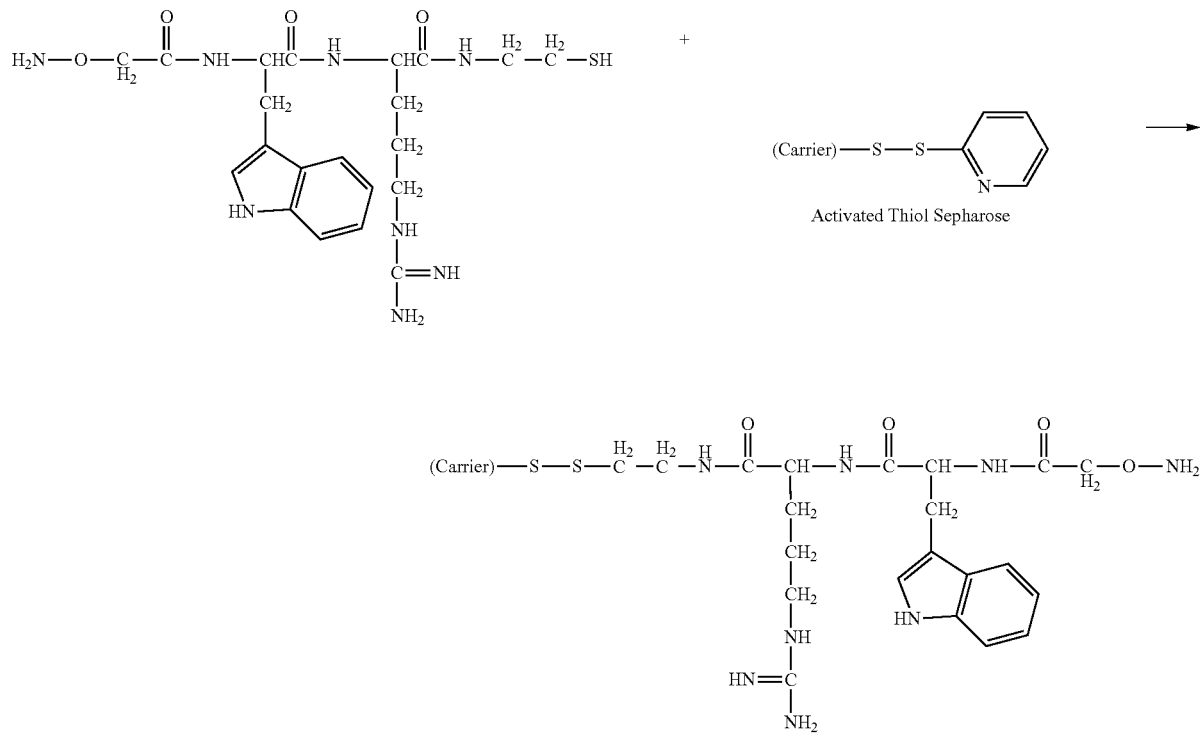

Activated Thiol Sepharose

In Scheme 1, a compound (b) is obtained by deprotection of a compound (a) in which an amino group in a tryptophan moiety is protected by a phenyl group or the like. Herein, the tryptophan moiety can also be substituted by phenylalanine, tyrosine, cysteine or the like.

Subsequently, a compound (d) is synthesized by the condensation reaction of a compound (b) with hydroxyamine (BocNHOCH$_2$COOH) (c) by a mixed anhydride procedure or the like. A protective group of this hydroxyamine is not restricted to Boc, and may be Fmoc, Troc or the like. Then, a compound (e) is obtained by the hydrolysis (saponification) of a methoxy group at a terminal end of the compound (d).

A condensation product (g) is synthesized by the action of 2-mercaptoethylamine (compound (f) on the compound (e), while a compound (h) is obtained by subjecting this condensation product (g) to a deprotection procedure. As this deprotection procedure, for example, when a protective group is Boc, a procedure by trifluoroacetic acid (TFA) can be cited.

Meanwhile, in the linker L of the above formula (1), a moiety containing chromophore or fluorophore may be formed by introducing a labeling functional group. Examples of the labeling functional group include aromatic residues having typical examples of a 2-aminobenzoyl group, a benzyl group, a naphthyl group, an anthracenyl group, a pyridyl group and the like; and substituents containing a Dansyl group or a Fmoc group. Furthermore, it may contain a deuterated (or not deuterated) acetyl group or the like, as described below.

As the sugar chain capture agent containing a 2-aminobenzoyl group, for example, in the above formula (1), there can be exemplified those in which a 2-aminobenzoyl group is contained in the linker L, and one sulfur of the disulfide bond has a structure derived from cysteine, for example, a structure of the following formula (3),

[Chemical Formula 15]

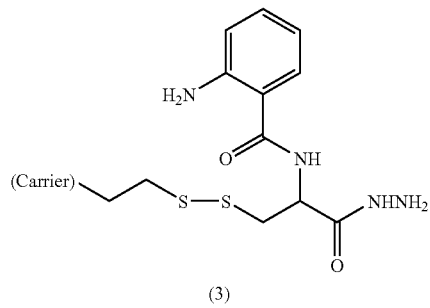

(3)

wherein, in the formula, the carrier is an inorganic substance or an organic polymer substance free from contributing to the sugar chain capture reaction.

Such a 2-aminobenzoyl group is a labeled compound for providing fluorescence, and is generally used for HPLC analysis of the sugar chain. Accordingly, a labeled sample with this group introduced into the sugar chain or the sugar derivative captured by using the sugar chain capture agent can be produced with ease. This labeled sample is used, whereby the sugar chain or the sugar derivative captured by using the sugar chain capture agent can be analyzed with high resolution and high sensitivity by HPLC employing a reverse phase column.

The sugar chain capture agent represented by the formula (3) can be obtained first by producing a compound (n) having a capture region and a linker region, as shown in the following Scheme 3, and subsequently, in Scheme 4, reacting with a carrier bonded, for example, to activated thiol sepharose, (Scheme 3)

[Chemical Formula 16]

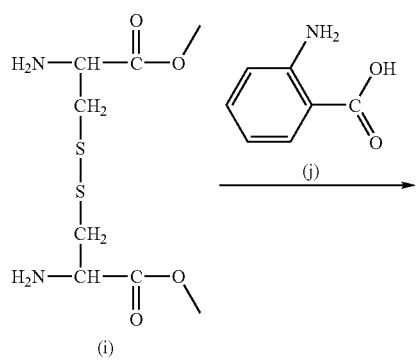

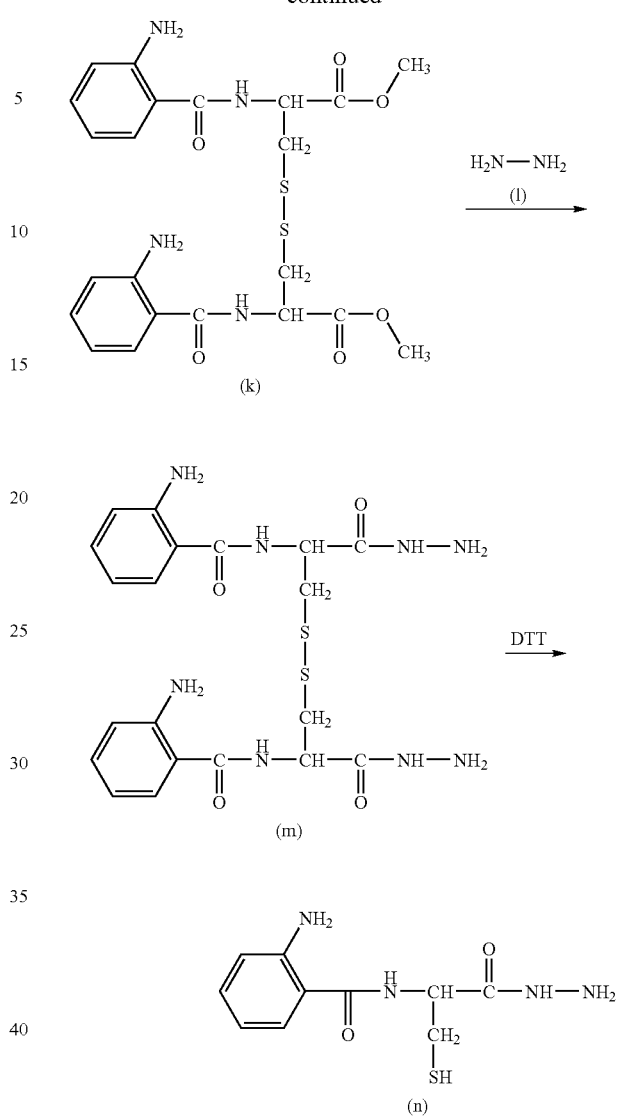

(Scheme 4)

[Chemical Formula 17]

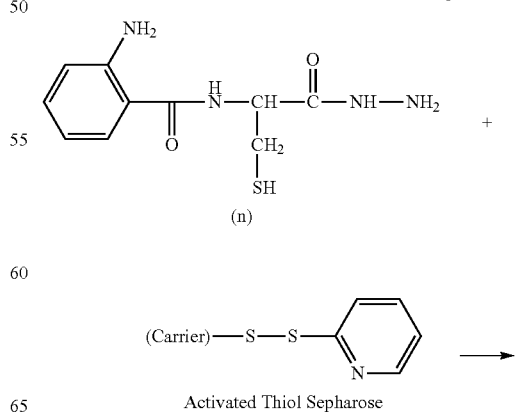

Activated Thiol Sepharose

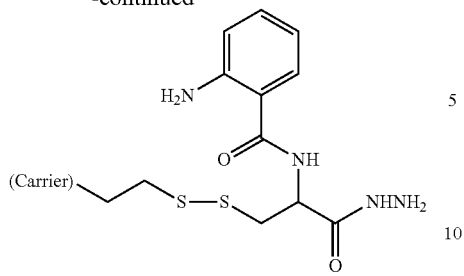

In Scheme 3, a compound (k) is obtained by reacting 2-aminobenzoic acid (compound (j)) with cysteine methyl ester (compound (i)) and form an amide bond between a nitrogen atom of the compound (i) and a carbonyl group of the compound (j). A compound (m) having an aminooxy group is obtained by reacting the compound (k) with hydrazine (compound (l)). Furthermore, a compound (n) containing an aminooxy group having a 2-aminobenzoyl group and cysteine is obtained by reducing the compound (m) using a reducing agent such as DTT or the like for cutting off the disulfide bond.

Meanwhile, as the sugar chain capture agent containing an acetyl group, there can be exemplified, for example, in the above formula (3), those having a structure in which a 2-aminobenzoyl group is modified with other functional groups, and those having a structure of the following formula (4) in the above formula (1),

[Chemical Formula 18]

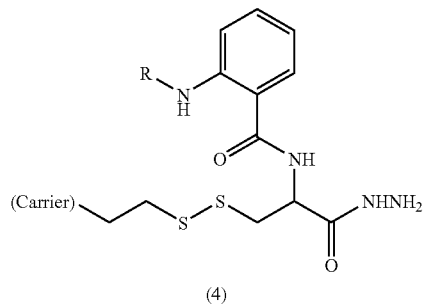

(4)

wherein, in the formula, R is a functional group capable of introducing via an amino group; and the carrier is an inorganic substance or an organic polymer substance free from contributing to the sugar chain capture reaction.

Examples of R include a protinated or deuteratedacetyl group, a protinated or deuterated succinyl group, a levulinoyl group and the like. Such examples are illustrated below,

[Chemical Formula 19]

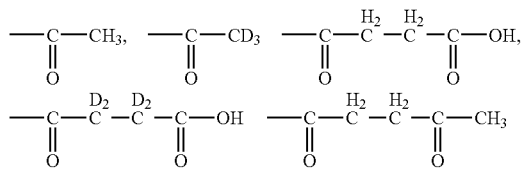

Of these compounds, compounds in which R is an acetyl group ($-COCH_3$) or a deuterated acetyl group ($-COCD_3$) can be suitably used. Namely, in the above formula (4), compounds having a structure of the following formula (5) or (6) can be used,

[Chemical Formula 20]

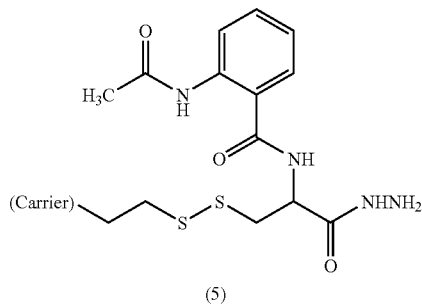

(5)

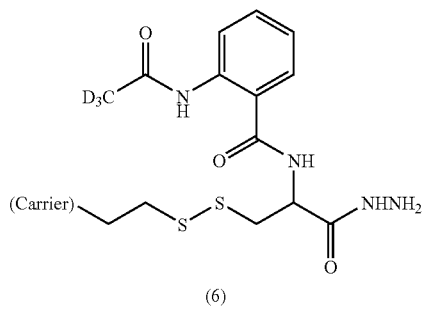

(6)

By introducing such an acetyl group, a labeled sample in which heavy hydrogen or light hydrogen is introduced into the captured sugar chain or the sugar derivative, that is, a deuterated or protinated sample can be easily produced.

The sugar chain capture agent illustrated in the formula (5) or (6) can be obtained first by producing a compound (s) having a capture region and a linker region prepared in Scheme 5 as shown below, and, in the aforementioned Scheme 4, reacting with a carrier bonded, for example, to activated thiol sepharose, (Scheme 5)

[Chemical Formula 21]

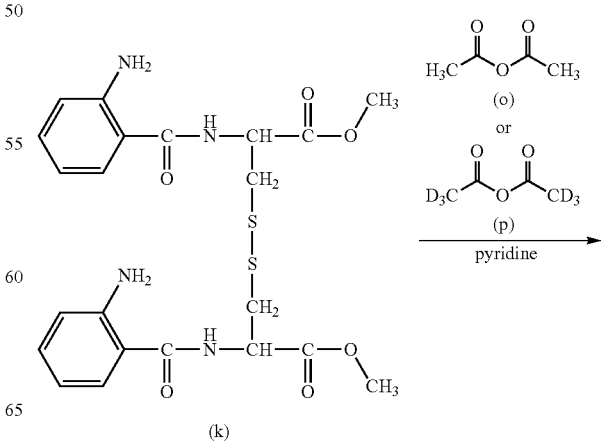

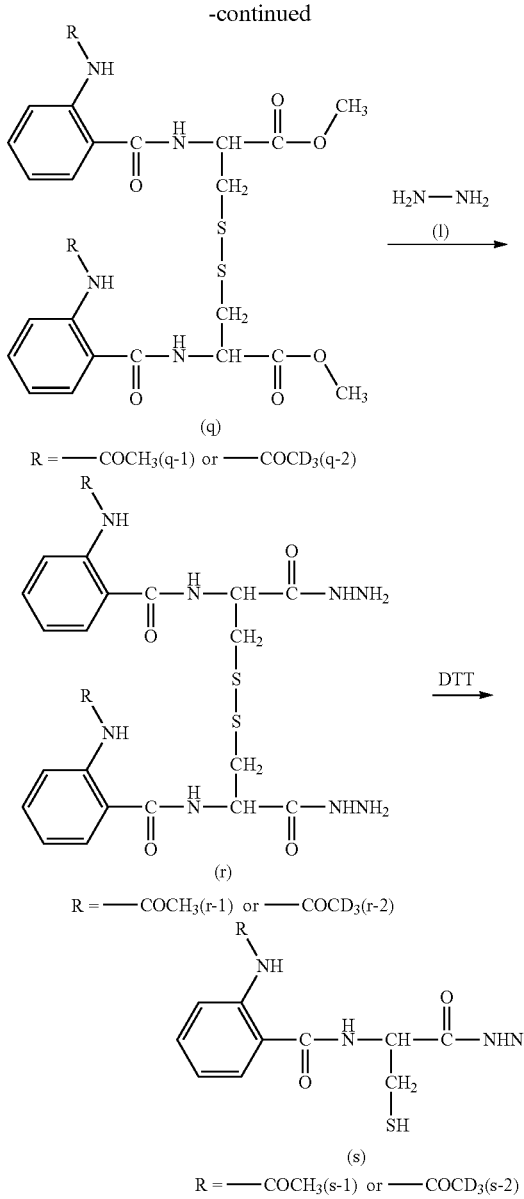

(q)

R = —COCH₃(q-1) or —COCD₃(q-2)

(r)

R = —COCH₃(r-1) or —COCD₃(r-2)

(s)

R = —COCH₃(s-1) or —COCD₃(s-2)

In Scheme 5, a compound (q) is obtained by the action of acetic anhydride on the compound (k) obtained in the aforementioned Scheme 3 and aceylating an amino group of a 2-aminobenzoyl group. At this time, a protinated compound (q-1) is obtained by using a compound (o) of acetic anhydride. On the other hand, a deuterated compound (q-2) is obtained by using a compound (p) of deuterated acetic anhydride.

Subsequently, a compound (r) having an aminooxy group is obtained by reacting the compound (q-1) or (q-2) with hydrazine. Incidentally, in the compound (r), when R is an acetyl group (—COCH₃), a hydride (r-1) is obtained, while, when R is a deuterated acetyl group (—COCD₃), a deuteride (r-2) is obtained.

Furthermore, a compound (s) containing an aminooxy group having a 2-aminobenzoyl group obtained by acetylating an amino group and cysteine by reducing to the compound (r) using a reducing agent such as DTT or the like, and cutting off the disulfide bond. Incidentally, in the compound (r), when R is an acetyl group (—COCH₃), a hydride (s-1) is obtained, while, when R is a deuterated acetyl group (—COCD₃), a deuteride (s-2) is obtained.

As described above, when such groups are introduced into the linker region L, the captured sugar chain can be detected with high accuracy and high sensitivity.

Furthermore, examples of the linker region L include an alkyl chain, and a group composed of a group containing an ester bond or an amide bond which is not labeled, in addition to the aforementioned labeled groups. For example, it may have a structure represented by the following formula, or combined structures of a plurality of structures freely selected from structures represented by the following formula (In the formula, n represents any integer),

[Chemical Formula 22]

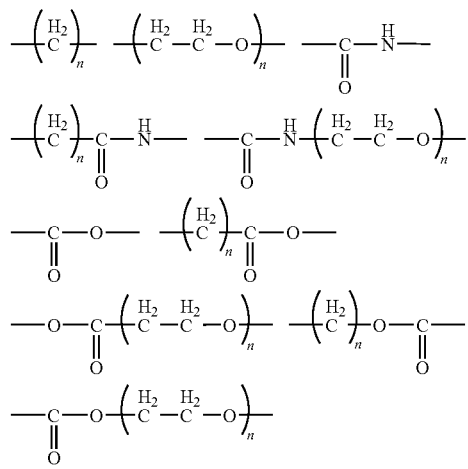

In this manner, by introducing the group which is not labeled into the linker region L, the sugar chain capture agent can be applied to a carrier composed of a solid phase substrate to be described below.

Furthermore, the carrier is an inorganic substance or an organic polymer substance, and is used in the form of a particle or a substance directly bonded to a solid phase substrate or a surface of the solid phase substrate.

Herein, as the inorganic substance which can be used as a carrier, a substance in the form of a particle can be used, and examples thereof include silica particles, alumina particles, glass particles, metal particles and the like.

Furthermore, examples of the organic polymer substance include polysaccharide gels having typical examples of agarose and sepharose, polymers of a vinyl compound in the form of a particle, and substances immobilized to a surface of the solid phase substrate. Further, the surface of the solid phase substrate may be formed by using these substances.

Meanwhile, the particle is preferably in the shape of a sphere, while the upper limit of its particle diameter is 200 μm and preferably 150 μm, and the lower limit is 20 μm and preferably 50 μm. Furthermore, the average particle diameter is from 80 to 100 μm. The particle of the carrier having a particle diameter in such a range is easily subjected to recovery by centrifugation, filter or the like, and the reaction efficiency with the sugar chain is also considered to be high because the particle has a sufficient surface area. When the particle diameter is vastly greater than the above range, the reaction efficiency with the sugar chain is lowered in some cases since the surface area becomes small. Furthermore, when the particle diameter is vastly smaller than the above range, it is particularly difficult to recover the particle by the filter in some cases. Further, when the particle is filled in a column and the particle diameter is too small, the pressure loss at the time of passing the fluid is high in some cases.

Furthermore, examples of the solid phase substrate include a microplate and a flat substrate. In this way, an analysis sample can be prepared by applying the sugar chain capture agent to a substrate for sugar chain microarrays.

Herein, the sugar chain capture reaction may be carried out by filling the aforementioned sugar chain capture agent in the form of a particle in a column or the like and passing through the pre-treated biological sample (continuous), or may be carried out by putting this particle into the pre-treated biological sample and stirring (batch). Furthermore, the reaction may be carried out by continuously putting the pre-treated biological sample into a reaction vessel filled with particles in advance and stirring (semi-batch).

Subsequently, in Step S30, the non-captured sugar chain by the sugar chain capture agent, other biological samples and the like are removed by washing the sugar chain capture agent after the completion of the sugar chain capture reaction in Step S20.

Herein, as the solvent used for washing of the sugar chain capture agent, there are used an aqueous solution of a surfactant having a typical example of sodium dodecyl sulfate (SDS); alcohol solvents such as methanol, ethanol and the like; water, an aqueous buffer solution and the like. Herein, when an aqueous solution is used for washing, the pH of the aqueous solution is preferably in the near-neutral region, and its pH is from 4 to 10 and more preferably from 6 to 8.

This washing treatment may be continuously conducted from the sugar chain capture reaction by passing through the cleaning solution to a column when the sugar chain capture reaction is continuously carried out as described above. Furthermore, in case of batch and semi-batch, substances other than the sugar chain capture agent may be removed by a filtering procedure or a centrifugal procedure.

Incidentally, the washing step of Step S30 may be carried out depending on the early state of the biological sample, for example, the degree of coexistence of substances other than the sugar chain.

In Step S40, after the completion of the washing treatment in Step S30, as necessary, when a compound containing a moiety capturing the sugar chain from the sugar chain capture agent is excised and released, that is, the aforementioned sugar chain capture agent is used, a reaction of excising the compound consisting of a linker region and a capture region from the sugar chain capture agent is carried out. At this time, the capture region contains both a region of capturing the sugar chain and a region free from capturing the sugar chain.

This reaction is a reaction of cutting off the disulfide bond contained in the sugar chain capture agent. According to this reaction, the carrier and the linker region are cut off with high reaction rate within a short period of time. Furthermore, for the reaction of cutting off this disulfide bond, a reducing agent may be used, and examples of the reducing agent which can be used include dithiothreitol, dithioerythritol, 2-mercaptoethanol, 2-mercaptoethylamine and the like. A solid phase reducing agent can be used for these reducing agents.

The reaction can be carried out in the near-neutral pH region and preferably in the pH of 6 to 9. The reaction can be carried out at a reaction temperature of from 4 to 90 degree centigrade, preferably from 25 to 90 degree centigrade and more preferably from 40 to 90 degree centigrade. The reaction is most preferably carried out in an aqueous solution of ammonium bicarbonate of 1 to 100 mM. Further, the reaction time is from 10 minutes to 24 hours, preferably from 10 minutes to 8 hours, and more preferably from 10 minutes to 2 hours.

Since, in the near-neutral pH region, a reaction of excising the sugar chain can be performed, the hydrolysis of the captured sugar chain, separation of the sialic acid residue or the like can be suppressed as compared to the conventional excising reaction of excising in the presence of a strong acid by trifluoroacetic acid.

Further, in the structure of the formula (1), a moiety of the disulfide (S—S) bond can be effectively cut off by the action of a reducing agent, so the releasing efficiency of the captured sugar chain can be high, and the sensitivity of the sugar chain analysis can be high.

In Step S50, the compound containing a capture region obtained by the excising reaction is separated from the carrier, a moiety of the compound containing a capture region is recovered, and the production of the analysis sample is completed. Examples of the recovery method include separation procedure such as centrifugation, filtering or the like.

In this way, the compound containing a capture region capturing the sugar chain is taken out. Incidentally, the compound containing a capture region free from capturing is also taken out together. However, since the identification of the sugar capture is not prevented and both compounds are easily separated, there is no special problem.

FIG. 2 is a block diagram illustrating a device to which the method for preparing an analysis sample according to the embodiment is applied. Incidentally, in explanation of each configuration, when each procedure of the flow chart in FIG. 1 is concerned, its step number is also indicated.

Into a biological sample introduction part 10 was introduced the pre-treated biological sample obtained by pre-treating the biological sample in a prescribed means (Step S10), and this biological sample is introduced into a reaction part 12 to be described below.

Into a cleaning solution introduction part 14 is introduced a cleaning solution when the reaction mixture after the aforementioned sugar chain capture reaction is washed (Step S30), and this cleaning solution is introduced into the reaction part 12 to be described below.

Into a reducing agent introduction part 16 is introduced a solution containing a reducing agent used in the excision step (Step S40) of the aforementioned sugar chain, and this solution of the reducing agent is introduced into the reaction part 12 to be described below.

The reaction part 12 is connected to the biological sample introduction part 10, the cleaning solution introduction part 14 and the reducing agent introduction part 16. Furthermore, for example, the aforementioned sugar chain capture agent in the form of a particle is filled in the reaction part 12. The moiety filled with this particle provides a site for carrying out the sugar chain capture step (Step S20), the washing step (Step S30) and the sugar chain excision step (Step S40).

An eluate extraction part 18 is arranged at an elution side of the reaction part 12, and is able to extract an eluate obtained by eluting a compound containing a capture region which is cut off from the carrier of the sugar chain capture agent from the reaction part 12 after the excision step (Step S40).

Into a separation part 20 was introduced the eluate obtained in the eluate extraction part 18. The separation part is to separate the compound containing a capture region and the carrier according to the aforementioned method. Incidentally, the separation part 20 is directly connected to the eluate extraction part 18. The eluate from the reaction part 12 may be directly introduced thereinto or the eluate obtained in the eluate extraction part 18 may be manually introduced.

According to this processing unit, the pre-treated biological sample is introduced into the reaction part 12 from the biological sample introduction part 10. In the reaction part 12, the introduced biological sample is maintained in the aforementioned conditions to perform the sugar chain capture reaction of capturing the sugar chain from the biological sample using the sugar chain capture agent (Step S20).

Subsequently, the cleaning solution is introduced into the reaction part 12 from the cleaning solution introduction part 14, a surface of the sugar chain capture agent after the completion of the sugar chain capture reaction is washed in the aforementioned conditions, and substances other than the non-captured sugar chain of the biological sample and unreacted sugar chain are washed down (Step S30).

Furthermore, a solution containing a reducing agent is introduced into the reaction part 12 from the reducing agent introduction part 16. On a surface of the sugar chain capture agent in the aforementioned conditions, a reaction of excising the compound containing a capture region is carried out, while the compound containing a capture region of the sugar chain capture agent is excised and eluted, and extracted at the eluate extraction part 18 (Step S40).

Subsequently, in the separation part 20, the compound containing a capture region and the carrier are separated from this eluate, and an analysis sample having the compound containing a capture region is obtained.

In this manner, when the sugar chain for an analysis sample is recovered and purified from the biological sample containing a sugar chain, the sugar chain is captured by using a sugar chain capture agent, the compound capturing this sugar chain is excised under mild conditions, for example, the sugar chain can be recovered without decomposing the captured sugar chain. Furthermore, in order to directly obtain an analysis sample having the compound containing a capture region capturing the sugar chain from the biological sample, identification and quantitative analysis of this sugar chain become easy.

Incidentally, the compound containing a capture region free from capturing is also taken out together. However, since the identification of the sugar capture is not prevented and both compounds are easily separated, there is no special problem.

Incidentally, in FIG. 2, a device formed such that a step of introducing a biological sample, a step of capturing a sugar chain (Step S20), a washing step (Step S30) and a sugar chain excising step (Step S40) are continuously carried out is explained, but not restricted thereto. For example, a particle composed of a sugar chain capture agent is introduced into the biological sample, shook or stirred. A reactant obtained by capturing a sugar chain with a sugar chain capture agent (Step S20) is filtered by applying to a filter, and on this filter, a cleaning solution is introduced for washing (Step S30), and then the reaction of excising (Step S40) may be carried out by the action of a reducing agent on the leached reactant. Incidentally, the aforementioned conditions can be applied to the conditions for carrying out procedures involved in each step.

Furthermore, the analysis sample according to the embodiment can be produced from the biological sample according to the aforementioned method for preparing an analysis sample. Specifically, the analysis sample contains a thiol group derived from a disulfide bond of the aforementioned sugar chain capture agent and a linker region, and it is obtained as a substance represented, for example, by the following formulae (t-1) and (t-2),

[Chemical Formula 23]

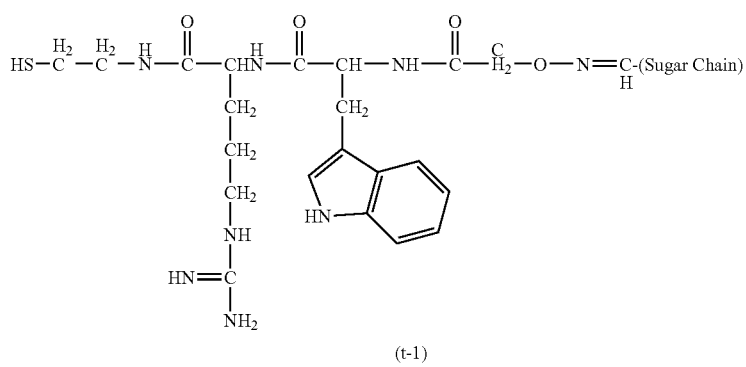

(t-1)

[Chemical Formula 24]

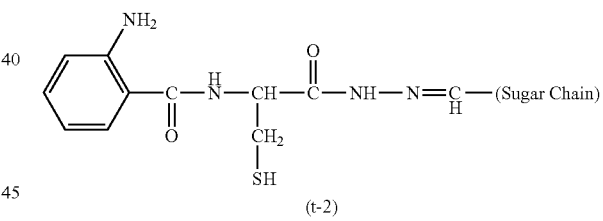

(t-2)

Accordingly, such an analysis sample contains peptide, a 2-aminobenzoyl group, a deuterated functional group and the like in the linker region. In particular, an analysis sample containing peptide is capable of enhancing the detection sensitivity by the aforementioned measurement of MALDI-TOFMS, while an analysis sample containing a 2-aminobenzoyl group enables HPLC analysis by detecting the aforementioned fluorescence.

Further, an analysis sample containing a deuterated functional group enables qualitative and quantitative analysis by enhancing the detection sensitivity by mass spectrometry.

For example, a deuterated sample by using a sugar chain capture agent of the compound (6) and a protinated sample by using the compound (5) are used in combination, whereby qualitative and quantitative analysis of the sugar chain contained, for example, in a sample containing an unknown sugar chain (for example, those obtained by treating human serum) can be performed by mass spectrometry.

Accordingly, for example, when a sample with a composition and concentration already known from the past is deuterium-labeled, an unknown sample is protium-labeled, and both samples are mixed and mass spectrometry is carried out, it is observed that each peak of the deuterated sample is shifted to the direction of high molecular weight as much as the number of introduced deuteriums rather than each peak corresponding to the protinated sample. Thereupon, the position (m/z value) and intensity of each peak are analyzed so that the kind of the sugar chain illustrated by each peak of the unknown sample and the concentration of the sample are found. Such analysis can be performed by making a known sample to a protium and an unknown sample to a deuterium.

Furthermore, in this analysis, a sample extracted from a healthy human is made to a deuterium, and a sample extracted from a disease patient is made to a protium, or a sample of a healthy human is made to a protium and a sample of a disease patient is made to a deuterium, whereby difference in the kind and amount of the sugar chain contained in both samples can be analyzed. Accordingly, such an analysis sample can be suitably used for purposes of the pathological diagnosis on the basis of a biological reaction participating in the sugar metabolism, medical treatment by suppressing such a biological reaction, and the like.

Furthermore, in the analysis sample of the embodiment, there is present a thiol group (—SH) derived from a disulfide bond in a molecule. A compound which is singularly reacted with this thiol group can be introduced into this analysis sample. For example, as this compound, an ICAT (Isotope Coded Affinity Tag) reagent is used, whereby the analysis sample of this embodiment can be applied to quantitative analysis according to the ICAT method.

EXAMPLES

The present invention is now illustrated below with reference to Examples including the following Experimental Examples. However, the present invention is not restricted to these Experimental Examples.

Experimental Example 1

Preparation of a Sugar Chain Capture Agent (1) Synthesis of a Compound Containing a Thiol Group and an Aminooxy Group According to the above Scheme 1, a compound (h) was synthesized.

(a) Synthesis of WR-OMe (Compound (b))

Methanol (5 ml) was added to Z—WR-OMe (10 mg, 20 mmol) and 10% Pd/C (10 mg), and the resulting mixture was stirred under a hydrogen gas atmosphere at room temperature for 2 hours. The reaction solution was filtered using an aqueous membrane filter, whereby Pd/C was removed, and the filtrate was concentrated under a reduced pressure, whereby a desired compound (b) (WR-OMe) was obtained. By the analysis according to MALDI-TOF-MS, a desired product, the [M+H]+ion was observed at m/z: 376.

(b) Synthesis of Boc-NHOCH$_2$CO—W—R-OMe (Compound (d))

A THF (6 ml) solution of Boc aminooxyacetic acid (2.5 mmol) was cooled down to −20 degree centigrade. Next, N-methylmorpholine (3.0 mmol) and isobutyl formate (3.0 mmol) were added thereto, and the resulting mixture was stirred for 15 minutes, whereby a mixed acid anhydride was prepared. The reaction solution was at a temperature of 0 degree centigrade, the compound (b) (WR-OMe (3.0 mmol)) was dissolved in water (3 ml) with another reaction solution, and sodium hydrogen carbonate (3.0 mmol) was added to prepare a WR-OMe solution. The WR-OMe solution was mixed and stirred for 1 hour. The reaction solution was concentrated under a reduced pressure, and the obtained residue was purified by silica gel column chromatography, whereby a desired compound (d) (Boc-NHOCH$_2$CO—W—R-OMe) was obtained. By the analysis according to MALDI-TOF-MS, a desired product, [M+H] ion, was observed at m/z: 547.

(c) Synthesis of Boc-NHOCH$_2$CO—W—R—OH (compound (e))

The compound (d) was treated with a sodium hydroxide/methanol solution and saponified to obtain a compound (e).

(d) Synthesis of Boc-NHOCH$_2$CO—W—R—NHCH$_2$CH$_2$SH (Compound (g))

The compound (e) was dissolved in methanol, and WSC (water-soluble carbodiimide) of 3 equivalents was added thereto. Aminoethanethiol (f) of 1 equivalent was added and stirred for 2 hours, whereby a condensation product was prepared. The reaction solution was purified by silica gel column chromatography, whereby a desired compound (g) was obtained.

(e) Synthesis of NH$_2$OCH$_2$CO—W—R—NHCH$_2$CH$_2$SH (Compound (h))

TFA (2 ml) was added to the compound (g), and the resulting mixture was stirred at −20 degree centigrade for 2 hours. The reaction solution was concentrated under a reduced pressure, toluene was added and the reaction solution was repeatedly azeotroped to remove TFA, whereby a desired compound (h) was obtained. By the analysis according to MALDI-TOF-MS, a desired product, [M+H] ion was observed at m/z: 493.

(2) Preparation of a Sugar Chain Capture Agent

According to the above Scheme 2, a solution of the compound (h) was mixed with Activated Thiol Sepharose (a product of Amersham Biosciences). The resulting mixture was allowed to stand at room temperature for 24 hours, and then an excess reagent was removed with pure water to obtain a sugar chain capture agent of the formula (2).

[Chemical Formula 25]

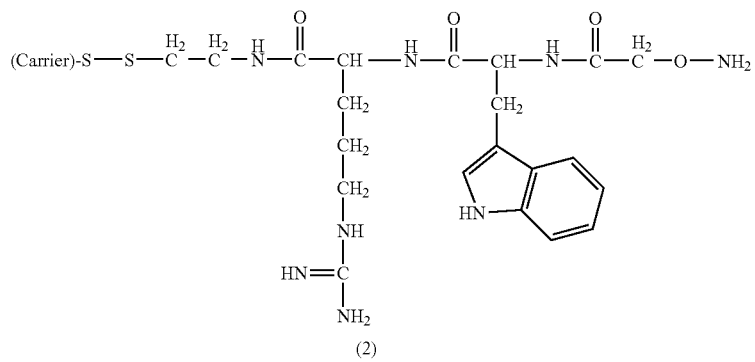

(2)

Experimental Example 2

Pre-Treatment of a Biological Sample

Normal human serum (5 μl) was trypsin-digested, whereby contained protein was fragmented into peptides. Trypsin was inactivated by heat denaturation, and then a sugar chain was released from peptide by peptide: N-glycanase F (a product of Roche) treatment. Furthermore, the pH was adjusted to 2 by hydrochloric acid, and the sugar chain was treated at 90 degree centigrade for 1 hour, whereby the sugar chain containing sialic acid was desialylated.

Sugar Chain Capture Reaction

A treated human serum was added to the sugar chain capture agent (10 mg) prepared in Experimental Example 1. The pH of the reaction solution was adjusted to 4 by using an acetic acid/sodium acetate buffer solution, and then the reaction solution was allowed to stand at 80 degree centigrade for 1 hour, whereby the sugar chain was bonded with a sugar chain capture agent.

Washing

The reactant after the sugar chain capture reaction was washed with 0.5% SDS, 50% methanol and pure water.

Sugar Chain Excising (Releasing) Reaction

To the reactant after washing was added 10 μl of 50 mM dithiothreitol, and the resulting mixture was allowed to stand at room temperature for 30 minutes. A filtrate containing a compound (t-1) of the following formula containing a capture region capturing a sugar chain by filtering with a filter and a moiety containing a carrier of a sugar chain capture agent were separated and a filtrate was recovered.

(a) Synthesis of (2-AB-Cys-OMe)$_2$ (Compound (k))

(Cys-OMe)$_2$ (3.4 g, 12.7 mmol) was dissolved in tetrahydrofuran (THF). Next, 2-aminobenzoic acid (2-aminobenzoic acid: (j)) (3.5 g, 25.4 mmol) and carbodiimidazole were added, and the resulting mixture was stirred at room temperature for 16 hours. The product was extracted and purified using a saturated solution of sodium hydrogen carbonate and sodium chloride, whereby a desired compound (k) ((2-AB-Cys-OMe)$_2$) was obtained. By the analysis according to MALDI-TOF-MS, a desired product, [M+H]+ion was observed at m/z: 507.

(b) Synthesis of (2-AB-Cys-CONHNH$_2$)$_2$ (Compound (m))

The compound (k) (5.0 mg, 9.9 mmol) and an excessive amount of hydrazine monohydrate were dissolved in methanol, and the resulting solution was stirred at room temperature for 16 hours, whereby a compound (m) was obtained.

(c) Synthesis of 2-AB-Cys-CONHNH$_2$ (Compound (n))

The compound (m) was dissolved in 100 mM DTT, 25 mM ammonium bicarbonate solution, and the resulting solution was stirred at room temperature for 1 hour. The product was purified by silica gel column chromatography, whereby a compound (n) was obtained. By the analysis according to MALDI-TOF-MS, a desired product, [M+H]+ion was observed at m/z: 255.

(2) Preparation of a Sugar Chain Capture Agent

According to the above Scheme 4, a water/acetonitrile solution of the compound (n) was mixed with Activated Thiol Sepharose (a product of Amersham Biosciences), and the resulting mixture was allowed to stand at room temperature for 24 hours, and then an excess reagent was removed with pure water to obtain a sugar chain capture agent of the formula (3),

[Chemical Formula 26]

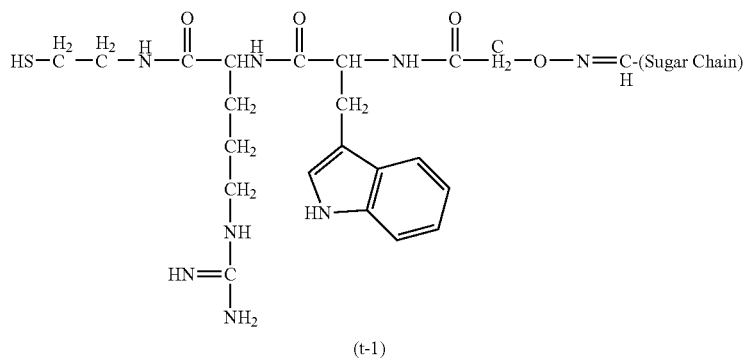

(t-1)

MALDI-TOF-MS Analysis

The filtrate was measured with MALDI-TOF-MS and as a result, as shown in FIG. 3, sharp peaks were observed at m/z values corresponding to molecular weights of the compound (h) added to the sugar chain captured from the human serum in the chart. In FIG. 3, the sugar chain assumed from m/z value was schematically illustrated for each peak. Incidentally, in FIG. 3, the structure of the labeled compound (h) of a reducing terminal was not illustrated.

Experimental Example 3

Preparation of a Sugar Chain Capture Agent (1) Synthesis of a Compound Containing a Thiol Group and an Aminooxy Group According to Scheme 3, a compound (n) was synthesized.

[Chemical Formula 27]

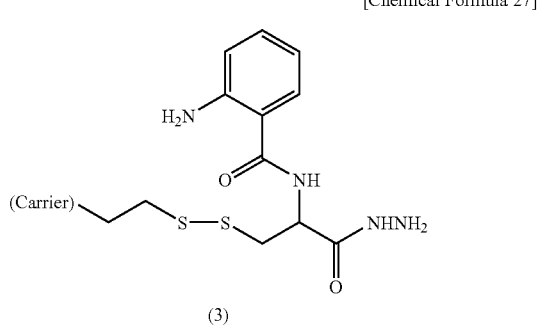

(3)

Experimental Example 4

Sugar Chain Capture Reaction

The sugar chain capture agent of the formula (3) was measured in a vessel such that the theoretical amount of the functional group was 300 nmol, and dispersed in acetonitrile containing 2% acetic acid. 50 μl of N-acetyl lactosamine (LacNAc) was added thereto, and the resulting mixture was heated at 80 degree centigrade for 1 hour, whereby LacNAc was captured with a sugar chain capture agent.

Sugar Chain Excising (Releasing) Reaction

To the reactant was added 20 μl of 100 mM dithiothreitol (DTT, 25 mM ammonium bicarbonate solution), and the resulting mixture was allowed to stand at 60 degree centigrade for 30 minutes. A filtrate containing a compound (t-2) of the following formula containing a capture region capturing a sugar chain by filtering with a filter and a moiety containing a carrier of a sugar chain capture agent were separated and a filtrate was recovered,

[Chemical Formula 28]

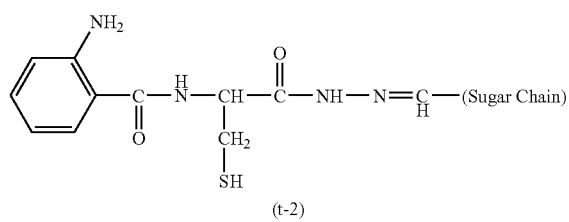

(t-2)

MALDI-TOF-MS Analysis

The filtrate was measured with MALDI-TOF-MS and as a result, as shown in FIG. 4, sharp peaks were observed at sites corresponding to molecular weights of the compound (n) added to LacNAc in the chart. In FIG. 4, a peak (A) is derived from the unreacted compound (n) free from capturing a sugar chain, a peak (B) is derived from the unreacted sugar chain (LacNAc) free from capturing, and a peak (C) is derived from the desired product capturing the sugar chain (LacNAc).

HPLC Analysis

The compound (t-2) separately prepared was measured by HPLC and as a result, a separation pattern was obtained as shown in FIG. 5. Each peak was taken out and analyzed by MALDI-TOF-MS and as a result, a peak corresponding to a molecular weight of the compound (t-2) at a peak position illustrated by an arrow in the Figure was observed.

Experimental Example 5

Preparation of a Sugar Chain Capture Agent (1) Synthesis of a Compound Containing a Thiol Group and an Aminooxy Group According to Scheme 5, a deuterium acetylated linker (compound (s-1)) was synthesized.

(a) Synthesis of a compound (q-1)

The compound (k) (5.0 g, 9.9 mmol) obtained in Experimental Example 3 was dissolved in pyridine. An excessive amount of acetic anhydride was added thereto, and the resulting mixture was stirred at room temperature for 16 hours, whereby a compound (q-1) was obtained.

(b) Synthesis of a Compound (r-1)

The compound (q-1) and hydrazine monohydrate were reacted in the same manner as in Experimental Example 3(1) (b) to obtain a compound (r-1).

(c) Synthesis of a Compound (s-1)

The compound (r-1) was treated with DTT in the same manner as in Experimental Example 3(1) (c) to obtain a compound (s-1). The obtained product was measured by MALDI-TOF-MS and as a result, a desired product, [M+H]+ ion was observed at m/z: 297.

(2) Preparation of a Sugar Chain Capture Agent

According to the above Scheme 4, a solution containing the compound (s-1) was mixed with Activated Thiol Sepharose (a product of Amersham Biosciences) to obtain a sugar chain capture agent of the formula (5).

Experimental Example 6

Preparation of a Sugar Chain Capture Agent (1) Synthesis of a Compound Containing a Thiol Group and an Aminooxy Group According to Scheme 5, a protium acetylated linker (compound (s-2)) was synthesized.

(a) Synthesis of a Compound (q-2)

The compound (k) (5.0 g, 9.9 mmol) obtained in Experimental Example 3 was dissolved in pyridine. An excessive amount of acetic anhydride-$d_6$ was added thereto, and the resulting mixture was stirred at room temperature for 16 hours, whereby a compound (q-2) was obtained.

(b) Synthesis of a Compound (r-2)

The compound (q-2) and hydrazine monohydrate were reacted in the same manner as in Experimental Example 3(1) (b), whereby a compound (r-2) was obtained.

(c) Synthesis of a Compound (s-2)

The compound (r-2) was treated with DTT in the same manner as in Experimental Example 3(1) (c) to obtain a compound (s-2). The obtained product was measured by MALDI-TOF-MS and as a result, a desired product, [M+H]+ ion was observed at m/z: 300.

(2) Preparation of a Sugar Chain Capture Agent

According to the above Scheme 4, a solution containing the compound (s-2) was mixed with Activated Thiol Sepharose (a product of Amersham Biosciences) to obtain a sugar chain capture agent of the formula (6),

[Chemical Formula 29]

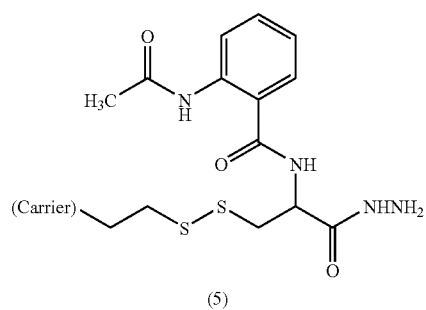

(5)

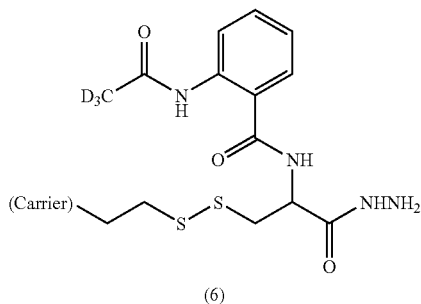

(6)

The invention claimed is:

1. A method for preparing an analysis sample comprising contacting a biological sample with a sugar chain capture agent, comprising the formula (Carrier)-S—S-Linker (L)-sugar capturing region (A), under conditions suitable to capture a compound with a sugar chain or sugar derivative, excising the compound containing a moiety capturing having the sugar chain and/or the sugar derivative from the carrier of sugar chain capture agent after the completion of the sugar chain capture reaction by severing the disulfide bond and releasing the compound, wherein the sugar chain capture agent is selected from the group consisting of

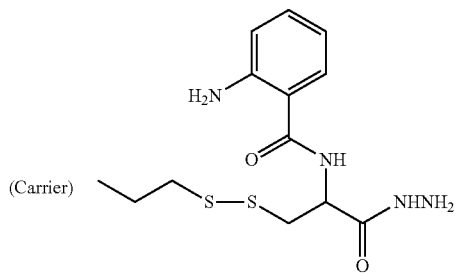

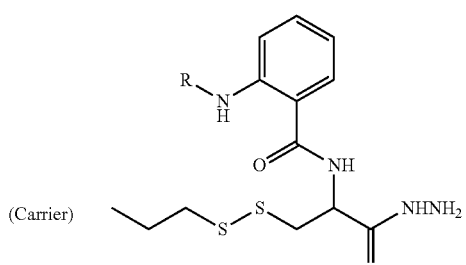

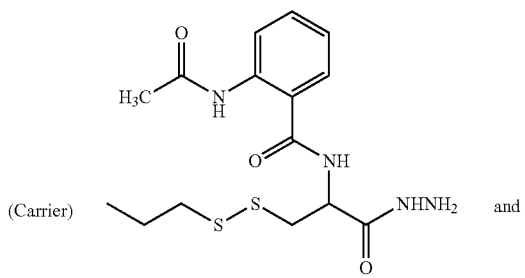

and

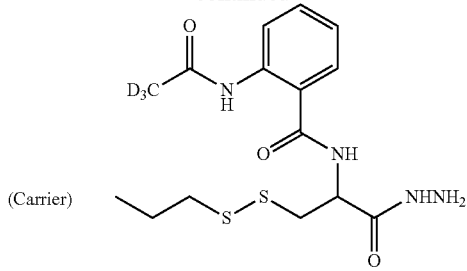

and wherein R is a functional group capable of reacting with an amino group.

2. A method for preparing an analysis sample according to claim 1 further comprising washing the sugar chain capture agent after the completion of the sugar chain capture reaction, and before the excision step.

3. The method for preparing an analysis sample as set forth in claim 1, wherein, the carrier is an inorganic substance or an organic polymer substance.

4. The method for preparing an analysis sample as set forth in claim 1, in which said sugar chain capture agent has a structure of the following formula,

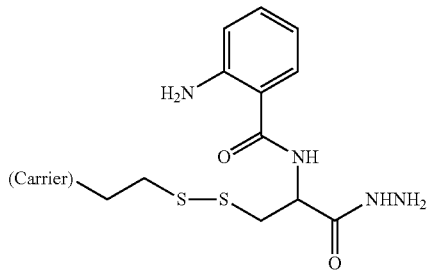

wherein, in the formula, the carrier is an inorganic substance or an organic polymer substance free from contributing to the sugar chain capture reaction.

5. The method for preparing an analysis sample as set forth in claim 1, in which said sugar chain capture agent has a structure of the following formula,

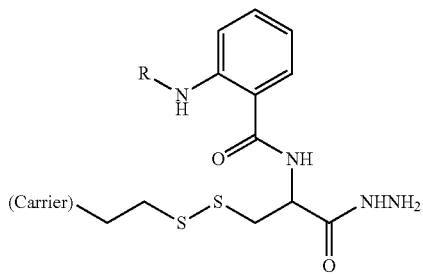

wherein, in the formula, R is a functional group capable of reacting with an amino group; and the carrier is an inorganic substance or an organic polymer substance free from contributing to the sugar chain capture reaction.

6. The method for preparing an analysis sample as set forth in claim 1, in which said sugar chain capture agent has a structure of the following formula,

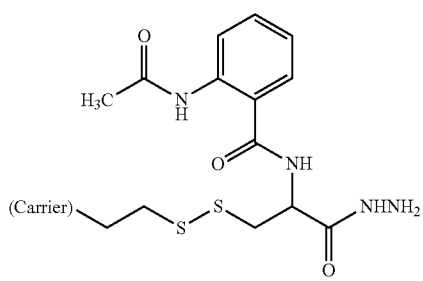

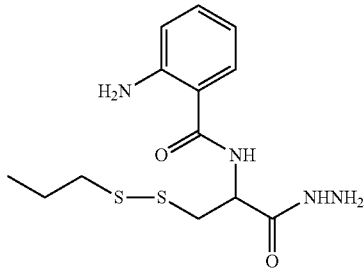

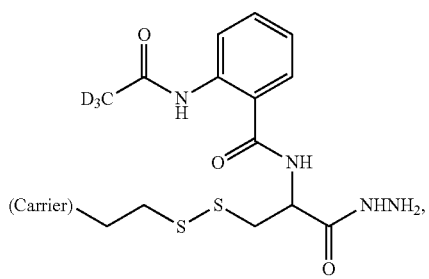

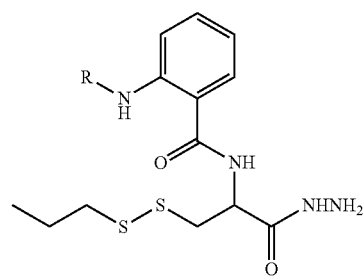

wherein the carrier is an inorganic substance or an organic polymer substance free from contributing to the sugar chain capture reaction.

7. The method for preparing an analysis sample as set forth in claim 1, wherein severing involves the action of a reducing agent.

8. The method for preparing an analysis sample as set forth in claim 1, in which the contacting step is carried out at a pH of 4 to 8.

9. The method for preparing an analysis sample as set forth in claim 1, wherein the excision step is carried out in the near-neutral pH condition.

10. The method for preparing an analysis sample as set forth in claim 1, wherein the carrier is a particle.

11. The method for preparing an analysis sample as set forth in claim 1, wherein the carrier is a solid phase substrate or a surface of the solid phase substrate.

12. A sugar chain capture agent having a structure represented by the following formula, (Carrier)-S—S-L-A wherein, in the formula, the carrier is an inorganic substance or an organic polymer substance free from contributing to the sugar chain capture reaction; L is a linker region; A is a capture region capturing the sugar chain; and —S—S is a disulfide bond and wherein the sugar chain capture agent is selected from the group consisting of:

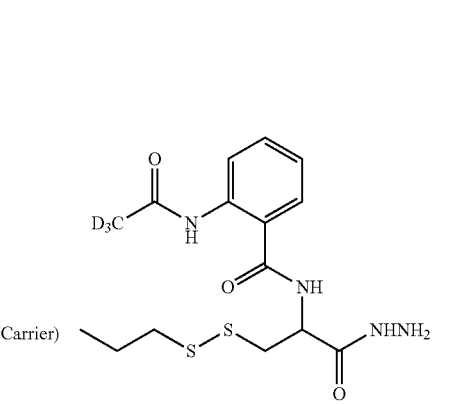

and wherein R is a functional group capable of reacting with an amino group.

13. The sugar chain capture agent as set forth in claim 12, having a structure of the following formula,

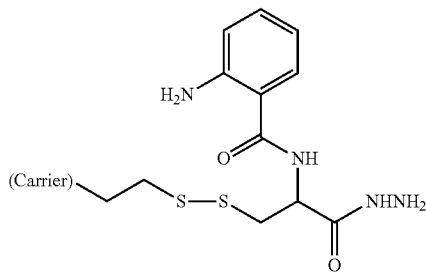

wherein the carrier is an inorganic substance or an organic polymer substance free from contributing to the sugar chain capture reaction.

14. The sugar chain capture agent as set forth in claim 12, having a structure of the following formula,

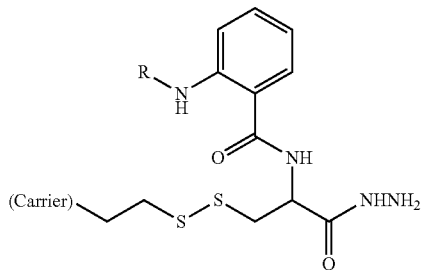

(4)

wherein, R is a functional group capable of reacting with an amino group; and the carrier is an inorganic substance or an organic polymer substance free from contributing to the sugar chain capture reaction.

15. The sugar chain capture agent as set forth in claim 14, having a structure of the following formula,

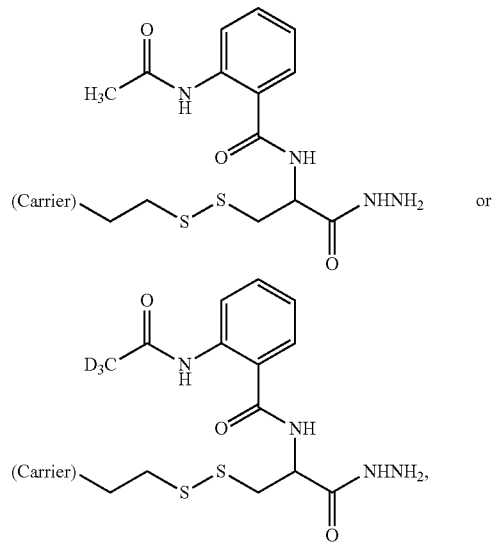

wherein the carrier is an inorganic substance or an organic polymer substance free from contributing to the sugar chain capture reaction.

16. The sugar chain capture agent as set forth in claim 12, wherein the carrier is a solid phase substrate or a surface of the solid phase substrate.

* * * * *